United States Patent [19]

Palomo-Coll

[11] Patent Number: 4,767,851

[45] Date of Patent: Aug. 30, 1988

[54] PROCESS FOR THE PREPARATION OF 7-AMINO AND 7-SUBSTITUTED AMINO-DESACETOXYCEPHALOSPORINS

[75] Inventor: Alberto Palomo-Coll, Barcelona, Spain

[73] Assignee: Gema, S.A., Barcelona, Spain

[21] Appl. No.: 752,897

[22] Filed: Jul. 8, 1985

[30] Foreign Application Priority Data

Jul. 16, 1984 [ES] Spain ............................... 534.339
Jul. 16, 1984 [ES] Spain ............................... 534.340
Jul. 27, 1984 [ES] Spain ............................... 534.646

[51] Int. Cl.$^4$ ............... C07D 205/08; A61K 31/545
[52] U.S. Cl. ............................... 540/218; 540/219; 540/330
[58] Field of Search ............... 540/218, 219, 230

[56] References Cited

U.S. PATENT DOCUMENTS 4,003,894  1/1977  Verweij et al. ............... 540/218
4,159,267  6/1979  Cheu ............................... 540/218

Primary Examiner—Nicholas S. Rizzo
Attorney, Agent, or Firm—Scully, Scott, Murphy & Presser

[57] ABSTRACT

An improved process is disclosed for the preparation of 7-amino and 7-substituted amino-desacetoxycephalosporins in which the corresponding 6-substituted amino penicillin sulphoxide is heated in the presence of an acidic substance which causes expansion of the penam ring in the reactant to the $\Delta^3$ cephem ring in the product in the presence of a silicon containing compound. The process comprises adding sulphamide or a silylsulphamide or a silylsulphamoyl to the reaction or utilizing a silylsulphamide or silylsulphamoyl as the silicon containing compound.

11 Claims, No Drawings

PROCESS FOR THE PREPARATION OF 7-AMINO AND 7-SUBSTITUTED AMINO-DESACETOXYCEPHALOSPORINS

BACKGROUND OF THE INVENTION

This invention relates to an improved process for the preparation of 7-amino and 7-substituted amino-desacetoxycephalosporins, of use in human and veterinary medicine.

Great importance has been attained by processes comprising the conversion of the five carbon atom heterocycle in a penicillin to a six atom heterocycle through the ring opening and ring formation sequence, which is promoted by heating a penicillin-sulphoxide solution.

PRIOR ART

The preferred methods use heat for ring opening and strong acids for ring formation. During this process, both the penicillin-sulphoxide and the corresponding resultant cephalosporin are decarboxylated, giving decomposition products which are biologically inactive.

To avoid the drawback of the formation of a cephalosporin without the carboxyl group, the use of alkyl esters has been disclosed in U.S. Pat. No. 3,275,626 and of silyl esters in U.S. Pat. Nos. 3,947,465, 4,000,129 and 4,003,894.

When using silylating agents for the ring expansion process in the formation of a cephalosporin, U.S. Pat. No. 4,003,894 teaches that the acidic compound must not be silylated under the reaction conditions required to form the thiazine ring. Therefore, amount must be adjusted, this being the reason for the decarboxylation. On the other hand, an excess of silylating agent eliminates the acidic compound by silylation, preventing ring formation, producing a dramatic reduction of the yield as shown by Verweij et al. (J. Org. Chem. 40(9), 1346, 1975).

Ring formation is necessary for producing a cephalosporin derivative. Thus, U.S. Pat. No. 3,275,626 (1966), teaches the use of acetic anhydride or p-toluenesulphonic acid. U.S. Pat. No. 4,003,894 teaches the use of strong acids to form organic base salts with an excess of the same organic base. Dutch patent application No. 2550/73 discloses ring formation with the use of inorganic Lewis acids, preferably sulphonic acids. According to the process disclosed in the former patent, a trimethylsilyl azetidinone-2-sulphenate is formed in a first stage using the silylating agents, produced by the ring opening caused by heat.

Overall, the process of converting a penicillin-(s)-oxide into a cephalosporin comprises the ring expansion of the five atom heterocycle to a six atom heterocycle through the following sequence: (a) ring opening and (b) ring formation. The process may be conducted in a single stage or in two stages, even with the isolation of the azetidinone intermediate as disclosed in the above mentioned Dutch application. The preferred methods use silylating agents to facilitate the ring opening with good yield, as disclosed in U.S. Pat. No. 4,003,894 and Dutch application No. 2550/73.

The main drawback of those processes is that the silylating agents react with the inorganic acids, sulphonic acids and salts of the acids with organic bases forming the corresponding silyl derivatives and losing their reactive capacity to produce ring formation. Furthermore, in the case of the salts, if the organic base is released in the reaction medium, this causes conversion of the $\Delta^3$ isomer into $\Delta^2$, this latter having no biological activity.

In view of the above, it is taught in U.S. Pat. No. 4,003,894 that the acidic compound should not be silylated under the reaction conditions. In the case of the Dutch application No. 2550/73, where sulphonic acids are preferred, these may not be used as such because they become very quickly silylated at a faster rate than the ring opening, and subsequently they do not produce the desired ring formation. Therefore, they must be used in a second stage in the absence of the initial silylating agent. This means having to use very closely adjusted amounts of silylating agent, favouring the reduction of yield (up to 80% loss). This loss, also occurs when an excess of silylating agent is ued to avoid decarboxylation.

When relatively large excesses of silylating agents are used, the amount of the acidic compound or salt thereof must be increased, causing losses which make the process more expensive, particularly since the recovery of the compounds required for the ring expansion, such as the sulphonic acids and the organic bases, which are extraordinarily soluble in water, is hard and complicated.

Belgian Pat. No. 747,120 and Austrian Pat. No. 306,919, operating with 6-$\beta$-acylamino-(s)-$\beta$-oxidepenicillanic acid esters, disclose the use of pyridine salts with sulphonic acids and orthophosphoric acid alkyl ester derivatives. In this process, desiccating agents are used to remove the water formed during the reaction with the view to improving the yield. In these processes, the use of a silylating reagent is not effective for ring expansion, because it reacts with the said salts and forms a basic medium on eliminating the acidic compound, which is responsible for the formation of the thiazine ring proper to the cephalosporins.

SUMMARY OF THE INVENTION

The present invention is directed to an improved process for the preparation of 7-amino and 7-substituted amino-desacetoxycephalosporins by heating the corresponding 6-substituted amino penicillin sulphoxide in the presence of an acidic substance which causes expansion of the penam ring in the reactant to the $\Delta^3$ cephem ring in the product in the presence of a silicon containing compound, the improvement being characterized by adding sulphamide or a silylsulphamide or a silylsulphamoyl to the reaction or utilizing a silylsulphamide or silylsulphamoyl as the silicon containing compound, avoiding the decarboxylation, $\Delta^2$-cephem-isomerization and resinification.

Therefore, an object of the invention is a ring formation or ring expansion process produced by heat, in the presence, in either case, of silyl sulphamides or silyl sulphamates and an acidic substance formed by the salt of a hydrogen bromide and a pyridine carboxylic or pyrimidine carboxylic or diazine carboxylic acid, which is silylated in the reaction medium.

A further object is the use of sulphamide or a trimethylsilyl sulphamide in combination with an amount of trimethylsilyl-2-oxazolidinone and an acidic substance formed by isonicotinic acid hydrobromide.

A further object is the recovery, preparation and the recycling of the acidic substance in the ring formation or ring expansion process to produce a cephalosporanic acid.

DESCRIPTION OF THE INVENTION

The invention provides a process for the conversion of a compound selected from among an azetidine having the formula I or a penicillin-sulphoxide having the formula II given below:

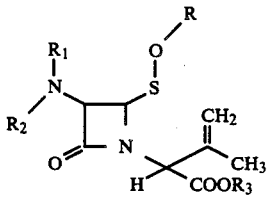 (I)

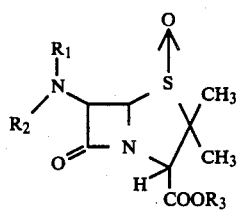 (II)

where:

R is an alkylsilyl, alkyl or a $C_2$–$C_5$ acyl group; $R_1$ is an atom of hydrogen or a group bound to the nitrogen atom by an atom of carbon or sulphur and optionally having substituents not affecting the reaction; $R_2$ is an atom of hydrogen or an acid residue having two to ten carbon atoms and which may include atoms of oxygen, sulphur or nitrogen and $R_1$ and $R_2$ together may be a phthalimido, oxazolidinyl, imidazolidinyl, formylidene, benzylidene or hydroxybenzylidene; $R_3$ is a group which may be removed by chemical or enzyme hydrolysis, from compounds which may form a further acidic substance in the reaction medium serving for the ring expansion reaction.

For R, a trimethylsilyl group is selected and when $R_1$ is an atom of hydrogen, $R_2$ is preferably an acyl group such as phenylacetyl, 2-thienylacetyl or phenoxyacetyl, or derivatives thereof substituted in the ring or in the alpha carbon.

$R_3$, for the formation of which there is released an acidic substance, may come from boron trichloride, aluminum trichloride, phosphorous trichloride, phosphorus tribromide, ethyleneglycol chlorophosphite, propyleneglycol chlorophosphite, ethyl dichlorophosphite. Acid halides such as benzyl chloroformate, acetyl bromide, trichloroacetyl chloride, pivaloyl chloride may be used. Also useful are silicon compounds comprising trimethylchlorosilane, dimethyldichlorosilane, methoxymethyldichlorosilane, butoxytrichlorosilane, trimethylbromosilane, triethoxychlorosilane, triethoxybromosilane, trimethoxychlorosilane. Sulphur derivatives such as thienyl chloride, thienyl bromide and ethyl and benzyl chlorosulphites may also be used.

$R_3$ may also be selected from groups which may undergo chemical or enzyme hydrolysis. Preferred substances are methyl, tert-butyl, cyclohexyl, phthalidyl, phenyl, benzyl, 2-tetrahydropyranyl and trimethylsilyl.

For the conversion of a formula I or formula II compound into a formula III compound:

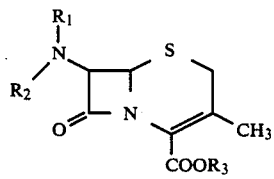 (III)

where $R_1$, $R_2$ and $R_3$ are as hereinbefore defined, the respective ring formation or ring expansion reactions are conducted preferably in presence of an acidic substance undergoing a substantial degree of silylation by heating the mixture to temperature of from 60° to 160° C., with a mixture formed by N-trimethylsilicon compounds preferably derived from a compound having the sulphamide or sulphamoyl function with another one having the amide function.

For the thiazine ring formation process characterizing a 7-substituted-aminodesacetoxycephalosporanic compound, a silicon compound having a sulphamide or sulphamate function selected from the group formed by N,N'-bis-trimethylsilylsulphamide, N,N,N',N'-tetrakis-trimethylsilylsulphamide, trimethylsilyl N,N-bis-trimethylsilylsulphamate, N,N,N',O-tetrakistrimethylsilylsulphamide, spiro-bis(1,1-dioxo-2,4-bis-trimethylsilyl)-1,$\lambda^6$,2,4,3-thiadiazasiletidine, 1,3-bis-dimethylsulphamoyl-2,4-tetramethylcyclodisilazane is preferred. The preparation of these compounds is described in the literature by M. Becke-Goehring et al. (Ann. Chemie 618, 43–52, 1958), W. Buss et al. (Z, Naturforsch. 30b, 482–846, 1975) and R. Appel et al. (Chem. Ber. 108, 1442–1446, 1975; Chem. Ber. 108, 2340–2348, 1975; Z. Naturforsch. 32b, 108, 1977).

The conversion of the formula I or II compounds into a formula III compound, together with the silicon products derived from a sulphamide or sulphamate, there may be used a combination with other silicon products of a carboxyamide selected from among N,O-bis-trimethylsilylacetamide, N,O-bis-trimethylsilyltrifluoroacetamide, N'-trimethylsilylacetamide, N-methyl-N-trimethylsilylacetamide, N-methyl-N-trimethylsilylformamide, N-trimethylsilyl-2-pyrrolidone,N-triethylsilylurea and N,N'-bis-trimethylsilylurea.

These silicon compounds produce in the medium products which do not interfere in the reaction or in the separation of the desacetoxycephalosporanic acid.

One convenient form of the invention comprises a mixture of N-trimethylsilyl-2-oxazolidinone (TMSO) with sulphamide or N,N'-bis-trimethylsilylsulphamide or a mixture of N,N'-bis-trimethylsilylurea with N,N'-bis-trimethylsilylsulphamide.

U.S. Pat. Nos. 3,947,465 and 4,072,710 disclose the preparation and use of TMSO as a new compound for use in silylation operations in the field of penicillins, cephalosporins and carboxylic acids in general. The use of TMSO in the ring expansion of penicillin-G gives a yield of 39%. Now the effectiveness of the TMSO-sulphamide or TMSO-bis-trimethylsilylsulphamide combination has been discovered. When the ring expansion takes place in the absence of TMSO, with sulphamide in the presence of pyridine hydrobromide, there is a dramatic decomposition and formation of resins. Conversely, with the TMSO sulphamide mixture, which is converted into trimethylsilylsulphamide, 7-phenylacetamido-desacetoxycephalosporanic acid is obtained with a 94% yield. Nevertheless, when portions of sulphamide were used as catalyst with TMSO, the result was a paste from which a 28% yield was obtained after a laborious treatment.

A practical process consists of the reaction of 6-aminopenicillanic (s)-oxide acid with TMSO in dichloromethane in presence of one equivalent of pyridine. There is added to the solution obtained phenacetyl chloride or bromide, with cooling in ice bath. The result is a solution of the compound of formula II containing in the medium the pyridine hydrochloride or hydrobromide necessary for the ring formation process. To this solution there is added toluene and more silylating agent with sulphamide or a bis-trimethyl-silyl sulphamide and a head fraction is distilled, to collect the dichloromethane, until a temperature of 100° to 120° C. is obtained in the reaction mass. The 6-aminopenicillanic (s)-oxide acid, like the penicillin sulphoxides, may be prepared following one of the processes disclosed in Spanish Pat. No. 509.855.

The silylating agents comprise TMSO/sulphamide, TMSO-N,N'-bis-trimethylsilylsulphamide and N,N'-bis-trimethylsilylsulphamide in amounts comprising the mole ratio of at least three silyl groups per penicillin sulphoxide in form of acid or pyridinium salt.

Azetidines and 6-substituted-penicillanic-sulphoxide acids which may be used for the purposes of the invention comprise those of formula I and II in which the:

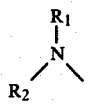

group may be a benzyloxycarbonylamido, phenylacetamido, phenoxyacetamido, 2-phenoxypropionamido, 3-acetylureido, 2-phenoxyphenylacetamido, 5-methyl-3-phenyl-4-isoxazolcarboxyamido, 5-methyl-3(o-chlorophenyl)-4-isoxazolcarboxyamido, 5-methyl-3-(2,6-dichlorophenyl)-4-isoxazolcarboxyamido, 2,6-dimethoxybenzamido, alpha-aminophenylacetamido, alpha-amino-2-thienylacetamido, 2-thienylacetamido, 2-furylacetamido, 2-tetrazolylacetamido, alpha-amino-p-hydrophenylacetamido. The preferred groups are phenylacetamido, 2-thienylacetamido and phenoxyacetamido.

The so-called acidic substance used both for the ring formation of the compound of formula I and for the ring expansion of the compound of formula II is hydrogen chloride or hydrogen bromide, the latter being the preferred one. This acid is incorporated in the reaction mass as such or combined with an organic base. Among these bases there are comprised the aliphatic, cycloaliphatic, aromatic and heterocyclic amines such as hexamethylenetetramine, diphenylamine, N-methylaniline, N-methylimidazol, isoquinoline, quinoline, pyridine or the substituted derivatives thereof, for example, the picolines, lutidines and cholidines. Although the preferred bases are pyridine and substituted pyridines, they form a group of acidic compound salts which may be silylated with the silylating agent. Therefore, for the advantage represented by the pyridine, pyrimidine or diazine carboxylic compounds for the conversion of the compound of formula I or II into a formula III compound, the acidic substance is used as a salt formed by two acidic components; one of them, the hydrogen bromide and the other is selected from nicotinic, isonicotinic, isocinchomeronic, dipicolinic, pyrimidine carboxylic, pyrazine carboxylic or 5-pyrimidine carboxylic acids among others.

The characteristics of these acidic substances contrarily to other acids mentioned is that they must be silylated by the silylating agent of the reaction mixture. They are prepared by the usual processes, such as evaporation of the solvent used for the combination of at least one equivalent of hydrobromic acid with another equivalent of the heterocyclic compound carboxylic acid. Thus, for example, one process comprises mixing an aqueous hydrobromic acid solution and the corresponding amount of a pyridine or diazine carboxylic acid; the water is removed from the resulting solution by known methods and the isolated compound is dried.

Inert solvents appropriate for the purposes of the invention are selected from among acetonitrile, benzene, 1,2-dimethoxyethane, butyl acetate, chloroform, N,N-dimethylacetamide, carbon tetrachloride, tetrachloroethane, chlorobenzene, 1,4-dioxane, toluene, xylene; preferred solvents are tetrachloroethane, toluene or 1,4-dioxane or mixtures allowing selected reaction temperature between 100° and 115° C. to be attained.

The isolation of the formula III compound, the desired cephalosporin, is effected by known processing which give an organic phase and an aqueous phase. The cephalosporanic acid is isolated from the decanted aqueous phase or the corresponding cephalosporin ester from the organic phase. The aqueous liquors are concentrated and decoloured if necessary, adjusted to the isoelectric pH of the pyridine carboxylic acid, which precipitates out and is recovered by filtration and after prior conversion into hydrobromide, it is recycled in the process.

EXAMPLES

EXAMPLE 1

Phenylacetamido desacetoxycephalosporanic acid 0.5 ml of trimethylchlorosilane and 10.94 g (5.35 cmoles) of bis-trimethylsilylurea were added to a suspension of 5.00 g of penicillin G-(s)-oxide (purity: 97.5%; $H_2O_{KF}$: 0%; 1.39 cmoles) in 100 ml of toluene.

The reaction mixture was heated to reflux (108.5°C.) and stirred for 1 hour at this temperature to obtain a solution of the 2'-(trimethylsilyl-azetidine-1-yl 4-oxo-3-phenylacetamido-2-sulphenate)-3'-methyl-3'-butenoic acid silyl ester.

2.18 g (1.07 cmoles) of isonicotinic acid hydrobromide were added to the resulting solution which was stirred for a further 2 hours under reflux.

The solution was cooled to 25° C. and 40 ml of water were added. The pH was adjusted to 8.5 with $NH_4OH$ (4.0 ml, 25% $NH_3$), followed by stirring for 15 minutes and decantation.

The aqueous phase was cooled to 10° C. and 50 ml of dichloromethane were added.

The pH was adjusted to 0.5 by addition of hydrochloric acid (7.1 ml, purity: 37%), followed by stirring for 60 minutes at 10°–15° C., filtration and washing with water (10 ml) and dichloromethane (25 ml) to obtain 3.89 of the subject product with a purity of 98% by HPLC (yield: 84.2%) $(\alpha)_D^{20} = +190°$ (c=0.5% in 60% MeOH). IR(KBr)$\nu$max cm$^{-1}$=3275, 1762, 1700, 1652 and 1546.

The organic phase was separated from the filtration liquor by filtration, concentrated to a volume of 10–15 ml, the pH was adjusted to 4 with 5N NaOH, the solution was cooled to 0° to +5° C. and held for 5 hours at this temperature. It was filtered, washed with water (2 ml) and acetone to give 1.17 g of isonicotinic acid with a 99-100% purity (isonicotinic acid recovery yield=89%).

EXAMPLE 2

Phenylacetamido desacetoxycephalosporanic acid

A suspension of penicillin G-(s)-oxide (5.0 g, 1.427 cmoles) and TMSO (9.06 ml, 4.61 cmoles) in 100 ml of toluene was heated at 55° C. for 5 minutes, followed by the addition of isonicotinic acid hydrobromide (2.23 g, 1.094 cmoles) and bis-trimethylsilylurea (BSU, 2.2 g, 1.077 cmoles).

The mixture was heated with reflux for 165 minutes, to give an orange-coloured solution, with a portion of molten solid. Thereafter it was cooled to 40° C. and the organic phase was removed by decantation; to isolate the dark paste which was washed with more toluene.

A solution of sulphuric acid (1.45 ml) in water (29 ml) was added to the decanted organic liquors with good stirring to cause precipitation.

Thereafter, isopropanol (3 ml) was added and the mixture was stirred for 30 minutes at 30°-40° C. The solid was filtered, washed with toluene (10 ml), water-isopropanol (28:2.43 v/v) and n-hexane.

After drying it produced 3.37 g of the compound of the title, with a 70% yield and 98% purity.

The isonicotinic acid was recovered from the aqueous filter liquors by the usual process of Example 1.

EXAMPLE 3

Phenylacetamido desacetoxycephalosporanic acid 0.5 ml of trimethylchlorosilane, 2.10 g of isonicotinic acid hydrobromide, 10.94 g (5,35 cmoles) of bis-trimethylsilylurea (BSU) were added successively to a suspension of 5.00 g of penicillin G-(s)-oxide (97.5% purity, $H_2O_{KF}$ 0%, 1.39 cmoles) in 100 ml of toluene.

The resulting mixture was heated under reflux and stirred for 2 hours 45 minutes.

Thereafter it was cooled to 30° C. and there were added successively a solution of 96% $H_2SO_4$ (1.45 ml) in water (29 ml), over 15 minutes, and isopropanol (3.0 ml). The mixture was stirred for 30 minutes at 30°-35° C., was filtered and washed successively with toluene (10 ml), a solution of 2.4 ml of isopropanol in 28 ml of water and dried to give 4.35 g of solid. This was suspended in 50 ml of dichloromethane, stirred for 15 minutes at room temperature, filtered and washed with 20 ml of dichloromethane to give 4.09 of the product of the title with 98-99% purity (yield: 86.6%).

The organic phase was decanted from the liquors of the first filtration and the aqueous phase was adjusted to pH 4 with 2N NaOH and concentrated to a volume of 10-15 ml. It was cooled to 0° to +5° C., allowed to rest for 5 hours, filtered and washed with water (2 ml) and acetone to give 1.13 g of isonicotinic acid with 99-100% purity (isonicotinic acid recovery yield=89%).

EXAMPLE 4

Phenylacetamido desacetoxycephalosporanic acid

Following the previous Example, but replacing the isonicotinic acid hydrobromide by nicotinic acid hydrobromide (2.18 g, 1.07 cmoles), 3.74 g of the product of the title were obtained (yield: 81%), with a 98-99% purity.

The organic phase was decanted from the filtration liquors and the aqueous phase was adjusted to pH 4 with 2N NaOH, was concentrated to a volume of 10-15 ml, cooled to 0° to +5° C. and allowed to rest overnight at this temperature. It was filtered, washed with water (2 ml) and acetone (5 ml), dried to give 0.84 g of pure nicotinic acid (nicotinic acid recovery yield=64%).

EXAMPLE 5

Phenylacetamido desacetoxycephalosporanic acid 0.5 ml of trimethylchlorosilane, 10.94 g of bis-trimethylsilylurea and 2.64 g (1.07 cmoles) of isocinchomeronic acid hydrobromide was successively added to a suspension of 5.00 g of penicillin G-(s)-oxide (97.5% purity, $H_2O_{KF}$ 0%, 1.39 cmoles) in 100 ml of toluene.

The resulting mixture was heated to reflux to give a solution. The reaction was completed after 2 hours 45 minutes under reflux.

When the reaction was terminated, the mixture was cooled to 25° C. and water (38 ml) was added. The pH was adjusted to 8.5-8.6 by addition of NH$_4$OH (25% NH$_3$, 5.5 ml), followed by stirring for 5 minutes and decanting.

The aqueous phase was cooled to 10°-15° C., 50 ml of dichloromethane were added and the pH was adjusted to 0.5 with 37.5% HCl (14 ml).

The mixture was stirred for 60 minutes at 10°-15° C., was filtered and washed with water (10 ml) and dichloromethane (25 ml). The dry product was suspended in a mixture of acetone (50 ml) and water (3 ml). It was stirred for 20 minutes and filtered.

The solid obtained, 1.10 g, was isocinchomeronic acid.

The solvent was evaporated at reduced pressure from the filtration liquors to give 3.52 g of the product of the title with a 98-100% purity (yield: 76.2%).

The organic phase was decanted from the first filtration liquors and the aqueous phase was adjusted to pH 3.5 with 2N NaOH, was concentrated to a volume of 20-25 ml, cooled to 0° to +5° C. and filtered.

A further 0.54 g of isocinchomeronic acid was obtained. Total isocinchomeronic acid recovery yield=92%.

EXAMPLE 6

Phenylacetamido desacetoxycephalosporanic acid

Following Example 3, but replacing the isonicotinic acid hydrobromide by 2.19 g (1.07 cmoles) of pyrazine carboxylic acid hydrobromide, 3.79 g of the product of the title was obtained, with a purity evaluated by HPLC of 99% (yield: 81%).

By treatment of the filtered liquors similar to that described in Example 3, the pyrazine carboxylic acid was recovered with a yield of 55%.

EXAMPLE 7

Phenylacetamido desacetoxycephalosporanic acid

Following Example 3, but replacing the isonicotinic acid hydrobromide by 2.19 g (1.07 cmoles) of 4-pyrimidine carboxylic acid hydrobromide, the product of the title was obtained with a 72% yield.

4-pyrimidine carboxylic acid was recovered with a 70% yield.

EXAMPLE 8

Phenylacetamido desacetoxycephalosporanic acid

Following Example 6, but replacing the toluene by tetrachloroethane and conducting the reaction at 110°

C., the product of the title was obtained with a 78% yield. The isocinchomeronic acid was recovered from the aqueous phase in a similar way.

EXAMPLE 9

Phenylacetamido desacetoxycephalosporanic acid

Following Example 2, the N,N'-bis-trimethylsilylurea was removed for reaction with the isonicotinic acid hydrobromide and this compound was replaced by pyridine hydrobromide (2.14 g, 1.34 cmoles). Water (16.5 ml) was added to the mixture cooled to 40° C. and the pH was adjusted to 9.0 with ammonium hydroxide.

The aqueous phase was decanted and thereafter adjusted to pH 0.9 and the solid was filtered, washed with water (10 ml), dichloromethane (30 ml) and dried, to give 1.87 g of the compound of the title, with a 39.0% yield.

EXAMPLE 10

Phenylacetamido desacetoxycephalosporanic acid

Following Example 6, but replacing the toluene by chlorobenzene or xylene and conducting the reaction at 110° C., the product of the title was obtained with a similar yield and the pyrazine carboxylic acid was recovered with a similar yield.

EXAMPLE 11

7-phenylacetamido desacetoxycephalosporanic acid

Penicillin G-(s)-oxide (25.0 g, 7.13 cmoles) having a moisture content of not more than 0.1%, isonicotinic acid hydrobromide (10.5 g, 5.10 cmoles) and N,N'-bis-trimethylsilylsulphamide (55.1 g, 22.94 cmoles) were added successively to toluene (500 ml). The resulting suspension was heated with stirring over 15 minutes to 80° C. and for a further 15 minutes to 107°-108° C. and it was held under reflux for 165 minutes. Thereafter it was cooled to 30° C., water (110 ml) was added and it was stirred for 5 minutes at 30° C.

An aqueous sulphuric acid solution (35 ml water and 7.3 ml 96% acid) was added to the above mixture at 30° C. with stirring for 5 minutes, followed by isopropanol (15 ml), with a further 30 minutes stirring. The precipitate was filtered and washed successively with toluene (50 ml), a 14:12 (v/v) aqueous isopropanol solution and n-hexane. After drying, 25.5 g of product were obtained.

The above solid was suspended in dichloromethane (300 ml) and after stirring the mixture at room temperature for 30 minutes, it was filtered, washed with further dichloromethane (100 ml) and dried to give the compound of the title (17.5 g, yield=74.0%), with a 98% purity determined by HPLC.

The aqueous phase was treated as described in Example 1 to isolate the isonicotinic acid with similar yield.

EXAMPLE 12

Phenylacetamido desacetoxycephalosporanic acid 0.5 ml of trimethylchlorosilane, 8.02 g (3.92 cmoles) of BSU and 2.18 g of isonicotinic acid hydrobromide were added successively to a mixture of 4.87 of penicillin G-(s)-oxide symmetrical anhydride and 100 ml of toluene. The reaction mixture was heated to reflux over 30 minutes and the resulting solution was held under reflux for 2 hours 45 minutes and then cooled to 22° C. Water (20 ml) and 46 ml 1N NaOH were added. The mixture was stirred for 30 minutes at 25° C., to terminate with a pH of 8.5.

The organic phase was removed by decantation and 50 ml of dichloromethane were added to the aqueous phase, it was cooled to 10°-15° C. and 37.5% HCl was added to pH 0.5. The mixture was stirred for 60 minutes and filtered. It was washed with 10 ml of water and 25 ml of dichloromethane. 1.73 g of the product of the title (yield: 36.5%) were obtained with a 97-98% purity. Following Example 1, the isonicotinic acid was isolated from the aqueous phase with a similar yield.

EXAMPLE 13

Phenylacetamido desacetoxycephalosporanic acid 0.5 ml of trimethylchlorosilane, 9.48 g (4.64 cmoles) of bis-trimethylsilylurea and 6.20 g (1.43 cmol) of penicillin G-(s)-oxide 2-tetrahydropyran ester were added to suspension of 2.18 g of isonicotinic acid hydrobromide in 100 ml of toluene.

The resulting mixture was heated to reflux and held at this temperature for 3 hours.

When the reaction was terminated, the solvent was removed by evaporation at reduced pressure and 24 ml of glacial acetic acid, 12 ml of water and 1.45 ml of 96% $H_2SO_4$ were added to the residue, to give a solution with an insoluble paste residue. Stirring was continued for 30 minutes and 40 ml of dichloromethane were added.

The organic phase was decanted off, dried with anhydrous $Na_2SO_4$, the solvent was evaporated at reduced pressure and the mixture was solidified by addition of n-hexane and stirring (60 minutes) at room temperature. It was filtered, washed with n-hexane and dried to give 4.04 g of the product of the title, with a 96% purity (yield: 81.8%).

The isonicotinic acid was recovered from the aqueous phase in a similar way to that described in Example 1, with a 90% yield.

EXAMPLE 14

Phenylacetamido desacetoxycephalosporanic acid phthalidic ester 0.5 ml of trimethylchlorosilane, 2.18 g of isonicotinic acid hydrobromide and 8.02 g (3.92 cmoles) of bis-trimethylsilylurea were added to a suspension of 6.88 g of penicillin G-(s)-oxide phthalidic ester in 100 ml of toluene.

The resulting mixture was heated to reflux and held for 2 hours 30 minutes at this temperature.

When the reaction was terminated, the mass was cooled to 30°-35° C. and a solution of 1.46 ml of 96% $H_2SO_4$ in 29 ml of water was added. The addition was made over 15 minutes. The mixture was stirred for 30 minutes at 30°-35° C. and filtered. It was washed with 10 ml of toluene, 20 ml of water and n-hexane to provide 5.92 g of product, which was dissolved in 150 ml of dichloromethane, the insoluble residue was removed by filtration and evaporation of the solvent at reduced pressure gave 4.66 g of the product of the title, having a purity of 97-98% as defined by HPLC (yield: 70.3%). m.p.: 198°-213° C. (dec). IR (KBr)$\nu$ max cm$^{-1}$: 3270, 1762, 1725, 1640, 1525, 965.

The isonicotinic acid was recovered in a similar way to that described in Example 1 from the aqueous phase of the first filtration with 82% yield.

EXAMPLE 15

Phenylacetamido desacetoxycephalosporanic acid phthalidic ester 0.5 ml of trimethylchlorosilane and 8.02 g (3.92 cmoles) of bis-trimethylsilylurea were added to a suspension of 6.88 g of penicillin G-(s)-oxide phthalidic ester in 80 ml of toluene.

The resulting mixture was heated to reflux and held for 3 hours at this temperature to obtain a solution of 2'-(trimethylsilylazetidin-1-yl 4-oxo-3-phenylacetamido-2-sulphenate)-3'methyl-3'-butenoic acid phthalidic ester.

There was added 2.18 g of isonicotinic acid hydrobromide to this solution and it was held for 2 hours under reflux. It was cooled to 30°-35° C. The treatment of the solution following the method described in Example 14 gave 4.53 g of the product of the title (yield: 68.3%)

The isonicotinic acid was recovered with an 83% yield when the liquors were treated as described in Example 14.

EXAMPLE 16

Phenylacetamido desacetoxycephalosporanic acid methyl ester 0.5 ml of trimethylchlorosilane, 2.18 g of isonicotinic acid hydrobromide and 8.02 g of bis-trimethylsilylurea were added to suspension of 5.2 g (1.43 cmoles) of penicillin G-(s)-oxide methyl ester in 100 ml of toluene and the resulting mixture was heated to reflux and held for 2 hours 30 minutes at this temperature.

The mixture was cooled to 30°-35° C. and a solution of 1.46 ml of 96% $H_2SO_4$ in 29 ml of water was added. The mixture was stirred for 30 minutes at 30°-35° C. and filtered.

The mixture was washed with toluene (10 ml) and water (20 ml) to give 3.10 g of the product of the title (yield: 63%). m.p. 189°-192.5° C. IR (KBr) $\nu$ max cm$^{-1}$: 3290, 1770, 1725, 1646, 1535, 1380.

1.12 g of isonicotinic acid (recovery yield 85%) were recovered from the aqueous phase treated as described in Example 1.

EXAMPLE 17

Phenylacetamido desacetoxycephalosporanic acid

Following Example 1, but using 6.34 g of bis-trimethylsilylurea, 3.71 g of product with a 42% purity (yield 33%) were obtained.

EXAMPLE 18

Phenoxyacetamido desacetoxycephalosporanic acid

Following Example 3, but using 5.09 g (1.39 cmoles) of penicillin V-(s)-oxide, 4.06 g of the product of the title (yield: 84%) were obtained, the isonicotinic acid being recovered with an 87% yield.

EXAMPLE 19

2'-(trimethylsilyl-azetidine-1-yl 4-oxo-3-phenoxyacetamido-2-sulphenate)-3'-methyl-3'-butenoic acid methyl ester 3.0 g of N,N'-bis-trimethylsilylsulphamide and 0.1 ml of trimethylchlorosilane were added to a suspension of 5.28 g (1.39 cmoles) of 6-phenoxyacetamido penicillanic-(s)-oxide acid methyl ester in 100 ml of toluene.

The mixture was heated to reflux and the resulting solution was stirred for 2 hours at this temperature.

The mixture was cooled to 0° to +5° C., stirred for 2 hours and filtered.

The solvent was removed from the filtered liquors by low pressure evaporation and the resulting oil is the methyl ester of the compound of the title with a virtually quantitative yield.

H$^1$ NMR (CDCl$_3$) $\delta$(ppm): 0.04 (s, 9H), 2.05 (s, 3H), 3.75 (s, 3H), 4.52 (s, 2H), 5.05 (s, 2H), 5.45 (s, 1H), 5.65 (q, 1H), 6.14 (d, 1H), 7.83 (d, 1H).

EXAMPLE 20

7-amino desacetoxycephalosporanic acid 10.90 g of bis-trimethylsilylurea and 2.10 g of isonicotinic acid hydrobromide were added successively to a suspension of 4.44 g (1.39 cmoles) of $\alpha$-benzylidene-6-amino penicillanic-(s)-oxide acid in 100 ml of toluene and the resulting mixture was heated to reflux at 108° C. and stirred for 3 hours at this temperature.

The reaction mixture was cooled to 5°-10° C. and 20 ml of water were added, the pH was adjusted with 37% hydrochloric acid to pH 0.2 and the mixture was stirred for 30 minutes at 5°-10° C.

After decantation of the organic phase, the aqueous phase was decoloured for 15 minutes with 0.3 g of NORIT SIX-1 charcoal and filtered.

The solution obtained was adjusted to pH 3.1 by addition of NH$_4$OH (25% NH$_3$) and stirred for 60 minutes at 0° to +5° C., filtered, washed with water (5 ml) and acetone and dried to give 1.43 g of the product of the title (yield 48%).

The isonicotinic acid was recovered from the aqueous liquors as described in Example 1.

EXAMPLE 21

Isonicotinic acid hydrobromide 20 g of isonicotinic acid were suspended in 42 g of hydrobromic acid (48% purity) at 20° C. and 40 ml of water. The mixture was heated to 75° C. to provide a solution.

150 ml of toluene was added and the water azeotropically distilled off using a Dean-Stark apparatus. The resulting suspension was cooled to 20° C., filtered and washed with toluene and dried to give the product of the title with a quantitative yield. m.p.: 267°-268° C., H$_2$O$_{KF}$: 0%, %B calculated: 39.2%. Found: 39.1%. IR(KBr)$\nu$ max cm$^{-1}$: 1735, 1600, 1508, 1392, 1238.

In a similar way the hydrobromide of nicotinic, isoinchomeronic, pyrazine carboxylic, 4-pyrimidine carboxylic, 5-pyrimidine carboxylic acids was obtained. All of them were characterised by bromine analysis and bands of the carboxylic group in the IR spectra.

EXAMPLE 22

7-phenylacetamido desacetoxycephalosporanic acid

Penicillin G-(s)-oxide (25.0 g, 7.13 cmoles) having a moisture content of not more than 0.1%, pyridine hydrobromide (8.8 g), 3-trimethylsilyl-2-oxazolidinone (TMSO) (54.2 ml, 33.9 cmoles) and sulphamide (20.6 g, 21.4 cmoles) were added successively to toluene (500 ml). The resulting suspension was heated with stirring for 15 minutes to 80° C. and for a further 15 minutes to 107°-108° C. and was held under reflux for 165 minutes. Thereafter was cooled to 30° C., water was added (110 ml) and was stirred for 5 minutes at 30° C.

An aqueous sulphuric acid solution (35 ml of water and 7.3 ml of 96% acid) was added to the above mixture at 30° C. followed by stirring for 5 minutes and then isopropanol (50 ml) followed by a further 30 minutes stirring. The precipitate was filtered and washed successively with toluene (50 ml), a 14:12 (v/v) aqueous isopropanol solution and n-hexane. After drying, 22.9 g of product were obtained with gross yield of 96.6%.

The above solid was suspended in dichloromethane (300 ml) and after stirring the mixture at room temperature for 30 minutes, it was filtered, washed with a further amount of dichloromethane (100 ml) and dried to give the compound of the title (19.3 g, yield=81.4%), having a purity of 99% determined by HPLC, $(\alpha)_D^{20} = +190°$ (c=0.5%, 60% methanol). IR (KBr)$\nu$ max cm$^{-1}$ =3275, 1762, 1700, 1652 and 1546.

EXAMPLE 23

Phenoxyacetamido desacetoxycephalosporanic acid

Following Example 22, but replacing the penicillin G-(s)-oxide by the corresponding amount of penicillin V-(s)-oxide, the compound of the title was obtained with a similar yield and purity.

EXAMPLE 24

Phenylacetamido desacetoxycephalosporanic acid phthalidic ester 0.5 ml of trimethylchlorosilane, 1.71 g of pyridine hydrobromide and 9.43 g of N,N'-bis-trimethylsilylsulphamide were added successively to a suspension of 6.88 g of benzyl-penicillin sulphoxide phthalidic ester in 100 ml of toluene.

The reaction mixture was heated to reflux over 30 minutes and stirred for two hours 30 minutes at this temperature, was cooled to 30°–35° C. and there was added a solution of 1.46 ml of 96% H$_2$SO$_4$ in 29 ml of water. The addition was made over 15 minutes. The mixture was stirred for 30 minutes at 30°–35° C. and filtered. It was washed with toluene (10 ml), water (20 ml), n-hexane and dried. The thus obtained solid (5.89 g) was dissolved in dichloromethane, the insoluble residue was filtered off and the product of the title (5.00 g) was obtained by evaporation of the liquid at reduced pressure, with a 97–98% purity by HPLC. Yield: 75.5%; m.p. 198°–213° C. (dec.) IR (KBr)$\nu$ max cm$^{-1}$: 3270, 1762, 1725, 1640, 1525, 965.

EXAMPLE 25

Phenylacetamido desacetoxycephalosporanic acid methyl ester 5.2 g of benzyl-penicillin sulphoxide methyl ester were suspended in 100 ml of toluene and trimethylchlorosilane (0.5 ml), pyridine hydrobromide (1.71 g), sulphamide (4.10 g) and N-trimethylsilyl-2-oxazolidinone (10.05 g) were added successively.

The reaction mixture was heated to reflux and held for 2 hours 30 minutes at this temperature.

It was cooled to 30°–35° C. and a solution 1.46 ml of 96% H$_2$SO$_4$ in 29 ml of water was added. The mixture was stirred for 30 minutes at 30°–35° C. and filtered.

It was washed with toluene (10 ml), water (20 ml) and dried to give 3.44 g of the product of the title (yield: 70%). m.p.: 189°–192,5° C. IR (KBr)$\nu$ max cm$^{-1}$: 3290, 1770, 1725, 1646, 1535, 1380.

EXAMPLE 26

Phenylacetamido desacetoxycephalosporanic acid methyl ester

Following Example 25, but replacing the trimethylsilyl-2-oxazolidinone and the sulphamide by 3.44 g of N,N'-bis-trimethylsilylsulphamide, 3.44 g of the product of the title were obtained with a 70% yield.

EXAMPLE 27

Phenylacetamido desacetoxycephalosporanic acid 0.5 ml of trimethylchlorosilane, 10.05 g of N-trimethylsilyl-2-oxazolidinone, 4.10 g of sulphamide and 6.20 g (1.43 cmoles) of benzyl-penicillin sulphoxide 2-tetrahydropyran ester were added to a suspension of 1.71 g of pyridine hydrobromide in 100 ml of toluene.

The reaction mixture was heated to reflux and stirred for 3 hours at this temperature (107°–108° C.).

When the reaction was terminated, the solvent was evaporated at low pressure and 24 ml of glacial acetic acid, 12 ml of water, 1.45 ml of 96% H$_2$SO$_4$ were added to the residue.

The mixture was stirred for 30 minutes at room temperature and 40 ml of dichloromethane were added.

The mixture was decanted and the solvent was evaporated from the organic phase at low pressure, dried over anhydrous sodium sulphate.

N-hexane (50 ml) was added to the resulting residue which was then stirred for 60 minutes at room temperature.

The residue was filtered, washed with n-hexane and dried to give 4.19 g of the product of the title with a 96–97% purity (Yield: 85.6%).

EXAMPLE 28

Phenylacetamido desacetoxycephalosporanic acid

Following Example 27, but replacing the N-trimethylsilyl-2-oxazolidinone and sulphamide by 10.29 g of N,N'-bis-trimethylsilylsulphamide, 4.04 g of the product of the title were obtained with a 97–98% purity (yield: 83%).

EXAMPLE 29

Phenylacetamido desacetoxycephalosporanic acid phthalidic ester

Following Example 24, but replacing the pyridine hydrobromide by 2.10 g of isonicotinic acid hydrobromide and using 12.74 g of N,N'-bis-trimethylsilylsulphamide, the product of the title was obtained with a 75% yield.

EXAMPLE 30

Phenylacetamido desacetoxycephalosporanic acid methyl ester

Following Example 25, but replacing the pyridine hydrobromide by 2.10 g of isonicotinic acid hydrobromide, the product of the title was obtained with a 72% yield.

EXAMPLE 31

Phenoxyacetamido desacetoxycephalosporanic acid

Following Example 27, but replacing the penicillin G sulphoxide ester by the corresponding amount of penicillin V-sulphoxide, the compound of the title was obtained with a 90% yield and similar purity.

EXAMPLE 32

Phenylacetamido desacetoxycephalosporanic acid

Penicillin G-(s)-oxide (25.0 g; 7.19 cmoles), N,N'-bis-trimethylsilylsulphamide (55.6 g; 23.13 cmoles) and pyridine hydrobromide (8.5 g, 5.3 cmoles) were suspended in 500 ml of toluene. Thereafter the mixture was heated to reflux over 30 minutes with good stirring; after 15 minutes up to 80° C., a solution is obtained. Heating was maintained for 165 minutes. Thereafter the mixture was cooled to 30° C. and first water (110 ml) was added; stirring the mixture for 10 minutes at 30° C., followed by a further solution prepared with 7.3 ml of sulphuric acid in 35 ml of water, with stirring for 5 minutes at 30° C. and finally 15 ml of isopropanol, with stirring for a further 30 minutes at 28°–30° C.

The above mixture was filtered and washed successively with toluene (50 ml), an aqueous isopropanol solution (140/12 ml) and n-heptane. The solid was isolated and dried to give 22.4 g of the compound of the title with a 94.5% yield. The above product was suspended in 300 ml of dichloromethane and after stirring for 30 minutes at 20°–22° C., was filtered and washed with 100 ml of dichloromethane to give 20.5 g of the compound of the title with 1% moisture, 86.5% yield and an IR spectrum identical to that of the amount initially obtained and to that of a pure sample, purity by HPLC 98%, $(\alpha)_D^{20} = +190°$ (c=0.5%, 60% methanol).

EXAMPLE 33

Phenylacetamido desacetoxycephalosporanic acid (A) 5.83 g of N,N'-bis-trimethylsilylurea, 3.43 g of N,N'-bis-trimethylsilyl sulphamide and 1.71 g of pyridine hydrobromide were added successively to a suspension of 5.00 g of benzyl-pencillin sulphoxide in 100 ml of toluene.

The reaction mixture was heated to reflux and stirred for 3 hours at this temperature.

The mixture was cooled to 30° C., 22 ml of water were added, followed by stirring for 10 minutes at 30°–35° C. A solution of 1.5 ml of 96% $H_2SO_4$ in 7 ml of water was added, followed by stirring for 10 minutes and the subsequent addition of 3 ml of isopropyl alcohol.

The mixture was stirred for 30 minutes at 30°–35° C., was filtered and washed with toluene (10 ml) a solution of 2.4 ml of isopropyl alcohol in 28 ml of water and separately with n-hexane to give 4.36 g of the product of the title (yield: 92%).

The phenylacetamido desacetoxycephalosporanic acid content was determined in the aqueous phase by microbiological analysis, being 0.33 g (overall yield 99%).

(B) 10.5 g (30 mmoles) of benzyl penicillin sulphoxide, 3 ml of α-picoline (30.5 mmoles) and 5.22 g of α-picoline hydrobromide (30 mmoles) and 100 ml of toluene were added successively to a solution of 12.5 ml (51 mmoles) of N,O-bis-(trimethylsilyl)acetamide and 12.26 g (51 mmoles) of N,N'-bis-trimethylsilyl sulphamide in 95 ml of 1,4-dioxane.

The reaction mixture was heated to reflux and stirred for 4 hours.

The mixture was cooled to 20° C. and poured over 1500 ml of water previously cooled to 0° to +5° C.

Thereafter 650 ml of ethyl acetate and 50 ml of butyl acetate were added and the pH was adjusted to 7 with a solution of 4N potassium hydroxide.

The phases separated, were decanted and the aqueous phase was extracted with 300 ml of ethyl acetate and 50 ml of butyl acetate. The decanted organic phase was pooled with the one previously obtained and the combination was reextracted with 200 ml of a 0.75M aqueous potassium phosphate solution buffered to pH 7. The extract was added to the main aqueous solution containing 9.66 g of the potassium salt of $\Delta^3$-7-phenylacetamide desacetoxycephalosporanic acid (yield: 87%) titrated by microbiological analysis using Escherichia Coli as test microorganism.

(C) 1.05 g (3 mmoles) of benzyl-penicillin sulphoxide, 20 ml of dioxane, 1 ml (4 mmoles) of N,O-bis(trimethylsilyl)acetamide, 1.15 g (3 mmoles) of N,N,N',O-tetrakis-trimethylsilyl sulphamide, 0.522 g (3 mmoles) of α-picoline hydrobromide and 0.6 ml (6 mmoles) of α-picoline were mixed at room temperature.

The reaction mixture was heated to reflux and held 4 hours at this temperature (102° C.).

It was poured over 200 ml of an aqueous 0.75M potassium phosphate solution, bufffered to pH 7 and 50 ml of butyl acetate and after adjusting to pH 2, the aqueous phase was extracted twice with 100 ml of ethyl acetate.

The organic phase was dried over magnesium sulphate and evaporated at reduced pressure to give 1.05 g of a product which by RMP and UV titration contained 0.80 g of $\Delta^3$-7-phenylacetamido desacetoxycephalosporanic acid (yield: 80%).

(D) 1.05 g (3 mmoles) of benzyl-penicillin sulphoxide, 20 ml of toluene, 1.5 ml (6 mmoles) of N,O-bis-(trimethylsilyl)acetamide, 1.25 g (4 mmoles) of trimethylsilyl N,N-bis-trimethylsilylsulphamate, 0.6 ml (6 mmoles) of α-picoline and 0.52 g (3 mmoles) of α-picoline hydrobromide were mixed together.

The resulting mixture was heated to reflux and held for 4 hours.

It was then cooled to 20° C. and poured over 140 ml of a 0.75M potassium phosphate solution buffered to pH 7. The aqueous solution was washed with 40 ml of ethyl acetate and diluted with water to 200 ml.

The amount of $\Delta^3$-phenylacetamido-desacetoxycephalosporanic acid potassium salt in the aqueous solution was calculated by microbiological analysis using Escherichia Coli as test microorganism.

The yield obtained was 97.5%.

(E) 0.36 ml (4.5 mmoles) of pyridine were added to a suspension of 0.525 g (1.50 mmoles) of benzylpenicillin sulphoxide in 10 ml of dioxane and the resulting solution was cooled to 0° C. followed by the addition of 0.05 ml (0.5 mmole) of acetyl bromide and the reaction mixture was stirred for 30 minutes at 0° C. 0.49 ml (1.9 mmoles) of N,O-bis(trimethylsilyl)acetamide and 0.38 g (1.6 mmoles) of N,N'-bis-trimethylsilyl sulphamide were added. The mixture was heated to reflux and after 4 hours at reflux, the amount of $\Delta^3$-phenylacetamide desacetoxycephalosporanic acid formed, titrated by a microbiological analysis, was 95%.

(F) 0.36 ml (4.5 mmoles) of pyridine were added to a suspension of 0.525 g (1.50 mmoles) of benzyl-penicillin sulphoxide in 10 ml of dioxane and the resulting solution was cooled 0° C. followed by the addition of 0.22 ml (2.5 mmoles) of trimethylbromosilane. The reaction mixture was stirred for 30 minutes at 0° C. and 0.675 g (3.3 mmoles) of N,N'-bis-trimethylsilyl urea and 0.79 g (3.3 mmoles) of N,N'-bis-trimethylsilyl sulphamide were added, followed by heating to reflux and stirring for 3.5 hours at this temperature (101°–102° C.).

The amount of Δ³-7-phenylacetamido-desacetoxycephalosporanic acid formed, titrated by microbiological analysis, gives an 87% yield.

(G) 0.525 g (1.50 mmoles) of benzyl-penicillin sulphoxide, 0.61 g (3 mmoles) of N,N'-bis-trimethylsilyl urea and 1,01 g (2 mmoles) of spiro-bis-(1,1-dioxo 2,4-bis(-trimethylsilyl)-1,λ⁶,2,4,3-thiadiazasiletidine) were suspended in 10 ml dioxane. 0.35 g (2 mmoles) of α-picoline hydrobromide were added and it was heated under reflux for 4 hours. The amount of Δ³-7-phenylacetamido-desacetoxycephalosporanic acid formed, titrated as in Example (C) represents an 85% yield.

(H) 0.525 g (1.50 mmoles) of benzyl penicillin sulphoxide, 0.45 g (2.2 mmoles) of N,N'-bis-trimethylsilyl area and 0.67 g (2.8 mmoles) of N,N'-bis-trimethylsilyl sulphamide were suspended in 10 ml of butyl acetate, 0.23 ml (2.2 mmoles) of α-picoline and 0.2 ml (2.2 mmoles) of trimethylbromosilane were added.

After heating for 4 hours at 100° C., the yield of Δ³-7-phenylacetamido desacetoxycephalosporanic acid was titrated by microbiological analysis and gave 84%.

(I) 7-Phenylacetamido desacetoxycephalosporanic acid

A mixture of 0.525 g (1.50 mmoles) of benzyl-penicillin sulphoxide, 10 ml of toluene, 0.12 ml (1.5 mmoles) of pyridine, 0.97 ml (6 mmoles) of N-methyl-N-trimethylsilylacetamide, 1.17 g (3 mmoles) of N,N'-bis(morpholinosulphonyl)diamino dimethylsilane and 0.365 g (2.1 mmoles) of α-picoline hydrobromide were heated to 100°-102° C. and held for 3.5 hours at this temperature.

The yield of Δ³-phenylacetamido desacetoxycephalosporanic acid formed was titrated by microbiological analysis to be 87%.

(J) 1.27 ml (5 mmoles) of N,O-bis-trimethylsilylacetamide 1.44 g (6 mmoles) of N,N'-bis-trimethylsilyl sulphamide, 0.36 g (2.25 mmoles) of pyridine hydrobromide and 6 ml of a 0.5M solution of hydrobromic acid in dioxane were added to a suspension of 1.35 g (3 mmoles) of benzyl-penicillin sulphoxide cyclohexyl ammonium salt, in 15 ml of dioxane.

The reaction mixture was refluxed for 4 hours and the yield of Δ³-phenylacetamido desacetoxycephalosporanic acid was titrated by microbiological analysis (78%).

EXAMPLE 34

7-phenoxyacetamido desacetoxycephalosporanic acid 1.1 g (3 mmoles) of phenoxyacetamidopenicillin sulphoxide, 20 ml of dioxane, 1.25 ml (5 mmoles) of N,O-bis-trimethylsilylacetamide, 1.20 g (5 mmoles) of N,N'-bis-trimethylsilyl sulphamide, 0.6 ml (6 mmoles) of α-picoline and 0.52 g (3 mmoles) of α-picoline hydrobromide were mixed together.

The reaction mixture was heated under reflux for 4 hours and thereafter was treated as in Example 25, the yield being estimated by microbiological analysis using Escherichia Coli to be 82%.

What we claim is:

1. A process for the preparation of 7-amino and 7-substituted aminodesacetoxycephalosporins which comprises reacting an azetidine of Formula I or a penicillin sulphoxide of Formula II:

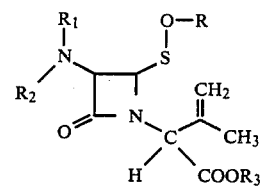

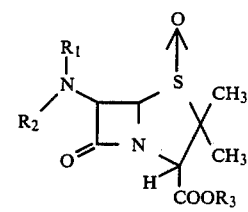

with a salt of an heterocyclic compound selected from the group consisting of pyridine carboxylic acids pyrimidine, pyrimidine carboxylic acids or diazine carboxylic acids in an inert solvent at a temperature ranging from about 60° C. to about 130° C. in the presence of a sufficient amount of an alkylsilyl sulphamide or an alkylsilyl sulphamoyl to effect the silylation of said salt, and forming the 7-acylamino-desacetoxycephalosporanic acid of the Formula III:

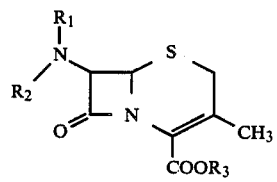

wherein R is an alkylsilyl, a $C_1$–$C_6$ alkyl or a $C_2$–$C_5$ acyl group, $R_1$ is hydrogen or a group bound to the nitrogen atom by an atom of carbon or sulphur and optionally with substituents, $R_2$ is hydrogen or an acid residue having two to ten atoms of carbon, which may include atoms of oxygen, sulphur or nitrogen and $R_1$ and $R_2$ together may be a phthalimido, oxazolidinyl, imidazolidinyl, formylidene, benzylidene or hydroxybenzylidene, and $R_3$ is hydrogen or a group selected from among methyl, tert-butyl, benzyl, phenyl, 5-indanyl, phthalidyl, 2-tetrahydropyranyl and trialkylsilyl having three to ten carbon atoms, or an easily chemically hydrolizable group obtained from the reaction of the penicillin-sulphoxide with a compound selected from the group consisting of trimethylbromosilane, trimethylchlorosilane, thionyl chloride, thionyl bromide, acetyl bromide, or pivaloyl chloride.

2. The process of claim 1, wherein a compound of formula II where $R_3$ is trimethylsilyl is prepared by heating in an inert organic solvent a penicillin-sulphoxide with a trialkylsilyl sulphamide or a trialkylsilyl sulphamoyl.

3. The process of claim 1, wherein said alkylsilyl sulphamide or said alkylsilyl sulphamoyl is selected from among N,N'-bis-trimethylsilyl sulphamide, N-trimethylsilyl sulphamide, N,N,N',N'-tetrakistrimethylsilyl sulphamide, N,O-bis-trimethylsilyl sulphamate, trimethylsilyl N,N,-bis-trimethylsilyl sulphamate.

4. The process of claim 3, wherein the reaction of a compound of formula I or II is conducted in the presence of a mixture of sulphamide or of an alkylsilyl sulphamide with a silyl compound selected from among the group comprising N-trimethylsilylurea, N,N'-bis-trimethylsilylurea, or N-trimethylsilyl-2-oxazolidinone.

5. The process of claim 4, wherein said mixture comprises at least 1 mole of a silyl compound per 0.5 mole of a silyl sulphamide compound and at the rate of from two to four moles of mixture per mole of compound of formula I or II.

6. The process of claim 4, wherein sulphamide is used with N-trimethylsilyl-2-oxazolidinone.

7. The procss of claim 6, wherein N,N'-bis-trimethylsilylsulphamide is used.

8. The process of claim 6, wherein N,N'-bis-trimethylsilylsulphamide is used with N,N'-bis-trimethylsilylurea.

9. The process of claim 1 wherein the heterocyclic salt is a hydrobromide or trifluoromethanesulfonate of nicotinic acid, isonicotinic acid, isocinchomeronic acid, 4-pyrimidine carboxylic acid, pyrazine carboxylic acid, 5-pyrimidine dicarboxylic acid and dipicolinic acid.

10. The process of claim 9, wherein isonicotinic acid hydrobromide is used.

11. The process of claim 1, wherein the inert solvent is selected from among toluene, xylene, chlorobenzene, 1,2-dichlorethane, 1,2-tetrachloroethane, 1,4-dioxane, acetonitrile, butyl acetate and N,N-dimethylacetamide.

* * * * *